(12) United States Patent
Kennedy et al.

(10) Patent No.: US 6,610,253 B2
(45) Date of Patent: *Aug. 26, 2003

(54) LIQUID PIN TRANSFER ASSEMBLY WITH COMMON PIN BIAS

(75) Inventors: Craig M. Kennedy, San Marcos, CA (US); Fernando J. Ramirez, Fountain Valley, CA (US)

(73) Assignee: Autosplice, Inc., San Diego, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 09/777,784

(22) Filed: Feb. 5, 2001

(65) Prior Publication Data

US 2001/0049149 A1 Dec. 6, 2001

Related U.S. Application Data

(63) Continuation-in-part of application No. 09/584,616, filed on May 31, 2000, now Pat. No. 6,579,499.

(51) Int. Cl.⁷ .............................. B01L 3/02; B01L 3/00; G01N 1/10
(52) U.S. Cl. .................. 422/100; 422/99; 436/180; 73/863.31; 73/863.32; 73/864; 73/864.01; 73/864.24
(58) Field of Search .................. 422/99, 100; 436/180; 73/863.31, 863.32, 864, 864.01, 864.24

(56) References Cited

U.S. PATENT DOCUMENTS

| | | | |
|---|---|---|---|
| 3,568,735 A | * | 3/1971 | Lancaster .................... 141/238 |
| 3,650,306 A | * | 3/1972 | Lancaster .................... 141/238 |
| 4,106,911 A | * | 8/1978 | Marcelli ...................... 422/63 |
| 4,158,035 A | * | 6/1979 | Haase et al. ............. 73/863.32 |
| 4,444,062 A | * | 4/1984 | Bennett et al. .......... 73/863.32 |
| 4,498,510 A | * | 2/1985 | Mihshew, Jr. et al. |
| 4,971,763 A | * | 11/1990 | Columbus |
| 5,660,792 A | * | 8/1997 | Koike |
| 5,756,050 A | * | 5/1998 | Ershow et al. |
| 5,827,745 A | * | 10/1998 | Astle |
| 5,882,930 A | * | 3/1999 | Baier |
| 5,962,329 A | * | 10/1999 | Ershov et al. |
| 5,976,470 A | * | 11/1999 | Maiefski et al. |
| 6,051,190 A | * | 4/2000 | Birch et al. |
| 6,238,626 B1 | * | 5/2001 | Higuchi et al. |
| 6,255,119 B1 | * | 7/2001 | Baier |
| 6,258,324 B1 | * | 7/2001 | Yiu |
| 6,309,891 B1 | * | 10/2001 | Shalon et al. |
| 2001/0008615 A1 | * | 7/2001 | Little et al. .................. 422/102 |
| 2001/0019845 A1 | * | 9/2001 | Bienert et al. ............... 436/181 |
| 2002/0009392 A1 | * | 1/2002 | Wolk et al. .................... 422/63 |
| 2002/0064887 A1 | * | 5/2002 | Shalon et al. ................ 436/180 |

* cited by examiner

Primary Examiner—Jill Warden
Assistant Examiner—Brian R Gordon

(57) ABSTRACT

Several pin transfer assemblies are disclosed that utilize the surface tension of liquids for picking up and dispensing minute volumes of liquid from wells in a first well plate to a flat substrate surface or into wells in a second well plate. In one embodiment, a plurality of pins reciprocate through complementary arrays of holes in a base plate and an overlying spring plate biased apart by coil springs located around the periphery of the base plate. A foam layer sits on top of the spring plate and a weight plate sits on top of the foam layer. A single coil spring is positioned between a center of the weight plate and the cover to push the weight plate downwardly. The periphery of the cover guides the vertical movement of the weight plate and is connected to the periphery of the base plate. The periphery of the base plate is supported by a frame used to register the pin assembly in a receptacle of a manual or automated liquid transfer apparatus.

22 Claims, 4 Drawing Sheets

LIQUID PIN TRANSFER ASSEMBLY WITH COMMON PIN BIAS

CROSS-REFERENCE TO RELATED APPLICATION

This application is a continuation-in-part of U.S. patent application Ser. No. 09/584,616, filed May 31, 2000 now U.S. Pat. No, 6,579,499, and entitled Liquid Compound Pin Replicator with Weight Bias.

BACKGROUND OF THE INVENTION

The present invention relates to methods and apparatus for preparing liquid compounds for chemical and biological analysis, and more particularly, to equipment for dispensing minute volumes of liquid onto a substrate surface or well in an array in connection with drug discovery and diagnostic analysis.

As the field of biotechnology has developed, traditional techniques for analyzing chemical structures, such as the use of pipettes to manually deposit small amounts of liquid, have become impractical. Automated devices have been developed, for example, to permit parallel processing protocols for DNA diagnostics. Robotic devices with multiple pipettes have been used, but they are slow and consume unnecessarily large amounts of expensive chemical assays. In one form of such a device a matrix of individual pins is attached to a robotic arm. The spacing of the pins in sufficient to allow their terminal lower ends to be dipped into corresponding wells of a well plate, thereby wetting the end of each pin with the sample liquid. The robotic arm then moves the pin matrix to the surface of a target substrate and contacts the end of each pin with the surface. The target substrate surface can either be flat or configured to provide a plurality of liquid receiving vessels or wells which themselves may have minute amounts of other liquids already deposited into the same. Thus the transfer of minute amounts of liquid with so-called pin replicator or pin transfer devices can be wet-to-dry or wet-to-wet.

The continual contact of delicate pins to a substrate surface or well bottom leads to wear which can introduce errors. In addition, the substrate surface or well bottoms at either the pick-up end or the deposit end may not be truly co-planar therefore causing fluid transfer errors. In addition, the pins may not all be the same length due to tolerance variations. U.S. Pat. No. 6,024,925 assigned to Sequenom, Inc. of San Diego discloses an improved pin transfer assembly that uses individually spring biased hollow pins. However, the structure of the Sequenom pin transfer assembly is relatively complex, unduly expensive and subject to mechanical failures.

SUMMARY OF THE INVENTION

It is therefore the primary object of the present invention to provide an improved pin replicator or pin transfer assembly for dispensing minute volumes of liquid onto a substrate surface or wells in an array in connection with drug discovery, diagnostic analysis, and other applications.

In accordance with the present invention, several pin transfer assemblies are disclosed that utilize the surface tension of liquids for transferring minute quantities of liquid between two different locations, e.g. by picking up and dispensing minute volumes of liquid from wells in a first well plate to a flat substrate surface or into wells in a second well plate. The pin transfer assemblies can be used in connection with automated drug discovery, diagnostic analysis, and other applications. In a first embodiment the pin transfer assembly comprises a base plate, a plurality of pins reciprocable through corresponding holes in the base plate, and a free floating weight plate resting on top of the upper ends of the pins. The weight plate biases the pins toward their fully extended lowered positions but and accommodates a lack of co-planarity at either the pick up end or the receiving end of the liquid transfer process. A cover attaches to the base plate, encloses the pins and weight plate and guides the weight plate during vertical movement thereof In a second embodiment, the pins reciprocate through complementary arrays of holes in the base plate and an overlying spring plate biased apart by coil springs located around the periphery of the base plate. A foam layer sits on top of the spring plate and a weight plate sits on top of the foam plate. A single spring is positioned between a center of the weight plate and the cover to push the weight plate downwardly. The periphery of the cover guides the vertical movement of the weight plate and is connected to the periphery of the base plate. The periphery of the base plate is supported by a frame used to register the pin assembly in a receptacle of a manual or automated liquid transfer apparatus. The pins are biased to an intermediate position between their fully extended lowered positions and their fully retracted raised positions. The foam layer ensures that the pins can accommodate non-co-planarity at the pick up or receiving ends of the liquid transfer process. In a third embodiment, the spring plate, weight plate and coil springs are eliminated. A foam layer is positioned between the array of reciprocable pins and the cover for biasing the pin heads toward the base plate.

DESCRIPTION OF THE PREFERRED EMBODIMENTS

Figure 1:
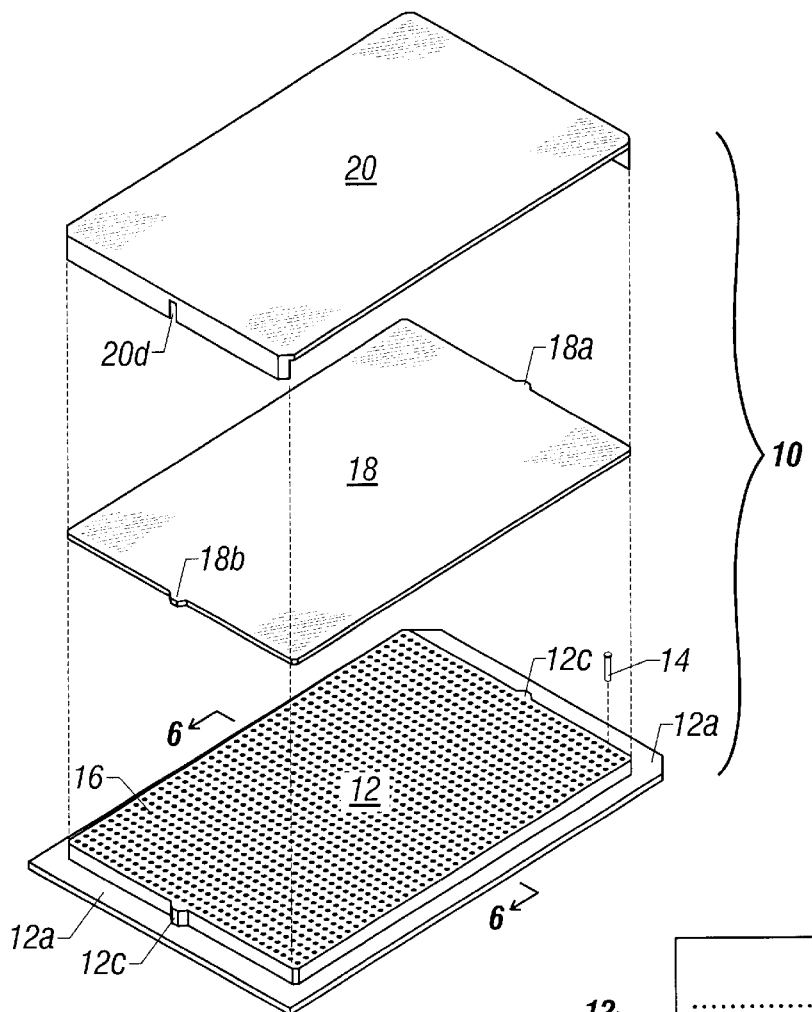
FIG. 1 is an exploded perspective view of a first embodiment of the pin transfer assembly of the present invention.
Figure 2:
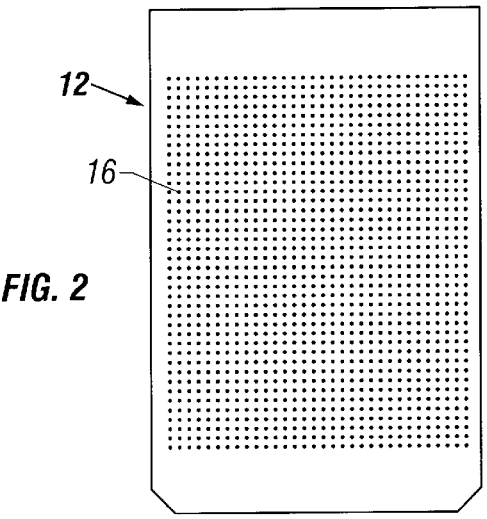
FIG. 2 is a plan view of the base plate of the pin transfer assembly of FIG. 1.

Referring to FIG. 1, a first embodiment 10 of a pin transfer assembly comprises a base plate 12, a plurality of pins 14 reciprocable through corresponding holes 16 in the base plate 12, and a free floating weight plate 18 resting on top of the upper ends of the pins 14. The weight plate 18 biases the pins 14 toward their fully extended lowered positions. A cover 20 attaches to the base plate 12, encloses the pins 14 and weight plate 18 and guides the weight plate 18 during vertical movement thereof The base plate 12, weight plate 18 and cover 20 each have a generally rectangular configuration. These components are preferably made of a suitable thermoplastic material so that they can be injection molded to provide the desired shape and dimensions. Where increased precision is necessary, the parts must be machined. The base plate 12 would be cut and holes 16 drilled. As shown in FIG. 2, the weight plate 20 may have holes 16 across substantially its entire surface to accommodate a large number of pins 14, such as one thousand five hundred and thirty-six pins. Alternatively, as show in FIG. 1, only the ends of the base plate 12 need have holes 16 formed therein to accommodate a smaller number of pins 14, such as two hundred and fifty-six pins 14.

Figure 4:
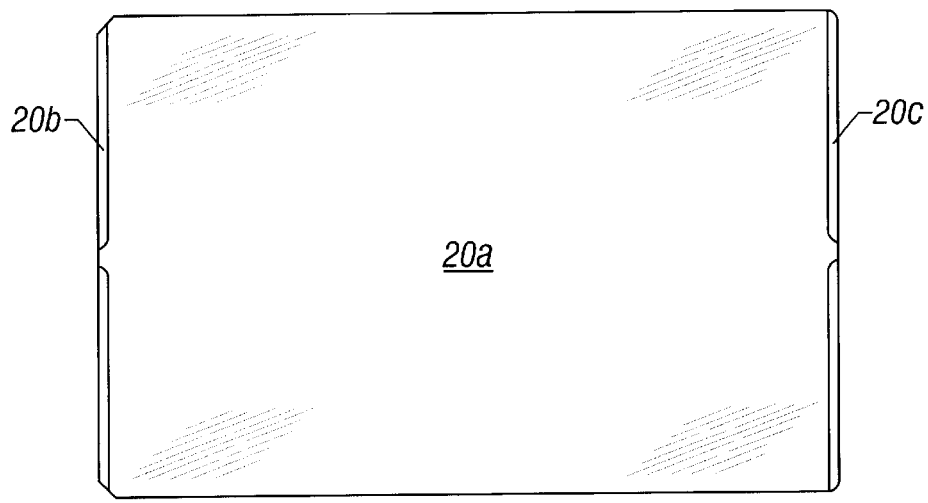
FIG. 4 is an enlarged bottom plan view of the cover of the pin transfer assembly of FIG. 1.
Figure 5:
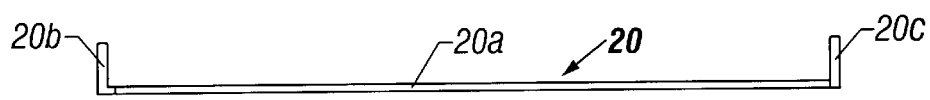
FIG. 5 is an enlarged side elevation view of the cover of the pin transfer assembly of FIG. 1.

The array of holes 16 in the base plate 12 provides a predetermined pattern of rows and columns. A periphery 12a (FIG. 1) of the base plate 12 extends beyond the cover 20 to provide a flange for predetermined alignment of the pin transfer assembly in a receptacle in a jig or automated system (not shown) into which the pin transfer assembly 10 can be loaded. The cover 20 includes a main horizontal planar section 20a (FIGS. 4 and 5) with two smaller vertical end walls 20b and 20c at each end. Preferably the medial portion 12b (FIG. 1) of the base plate 12 is raised compared to the periphery 12a to provide a shoulder over which the end walls 20b and 20c of the cover 20 may be snap fit to retain the base plate 12 and cover 20 together.

The upper end of each pin 14 (FIG. 3) comprises a head 14a that abuts the base plate 12 when the pin 14 is in its fully extended lowered position. The lower end 14b of each pin 14 is tapered to facilitate insertion through the corresponding hole 16 in the base plate 12. The weight plate 18 and the cover 20 include complementary projections and registration features that engage each other to guide the weight plate. These complementary projections and registration features include tabs 18a and 18b (FIG. 1) formed on the weight plate 18 and slots 20d (FIG. 1) formed on the cover 20 which slidingly receive the tabs 18a and 18b. The base plate 12 also has tabs 12c that engage the cover 20 to align the same.

Figure 6:
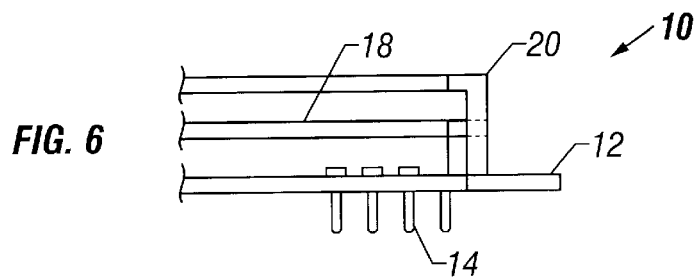
FIG. 6 is an enlarged fragmentary vertical sectional view of the pin transfer assembly taken along line 6—6 of FIG. 1.

FIG. 6 is an enlarged fragmentary vertical sectional view of the pin transfer assembly 10 taken along line 6—6 of FIG. 1. The pins 14 are shown in their fully extended lowered positions. However, the weight plate 18 is shown slightly raised off of the heads 14a of the pins for the sake of clarity.

Figure 7:
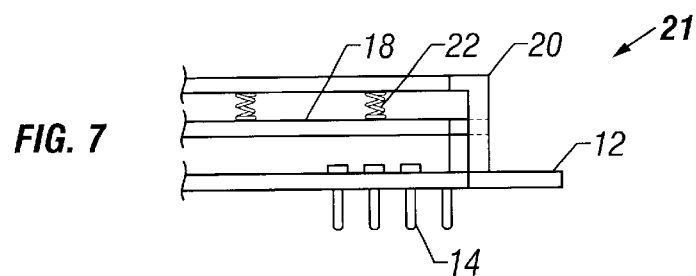
FIG. 7 is a view similar to FIG. 6 showing a modification of the first embodiment that includes coil springs for biasing its weight plate toward its base plate.

FIG. 7 illustrates a modification 21 of the pin transfer assembly of FIGS. 1–6 in which at least one coil spring 22 positioned between the weight plate 18 and the cover 20 for biasing the weight plate toward the base plate 12. This provides the advantage of allowing the pin transfer assembly to be inverted without the pins moving away from their fully extended positions.

In accordance with a novel liquid transfer method provided by the present invention, the pin transfer assembly 10 can be moved downwardly toward a first well plate (not shown) so that a lower end 14b of each of the pins 14 contacts the sample liquid in the corresponding well a sufficient amount to pick up and retain a small quantity of the sample liquid due to surface tension. The weight plate 18 serves to ensure co-planarity of the lower ends 14b of the pins 14 by pushing each pin 14 downwardly to its fully extended lowered position while allowing each pin 14 to move upwardly should it contact an upper surface of the corresponding well of the first well plate. The pin transfer assembly 10 can be moved upwardly away from the first well plate and laterally to a position above a flat substrate or second well plate (not shown). The pin transfer assembly 10 can then be moved downwardly toward the flat substrate or second well plate so that the lower end 14b of each of the pins 14 is sufficiently close to the flat substrate or a corresponding well of the second well plate so that the s all quantity of the sample liquid on the lower end 14b of each of the pins 14 contacts an upper surface of the flat substrate or the corresponding well of the second well plate. Thereafter the in transfer assembly 10 can be moved upwardly away from the flat substrate or second well plate and surface tension will cause a portion of the small quantity of the sample liquid previously carried by the lower end 14b of each of the pins 14 to remain on the flat substrate or in the corresponding well of the second well plate.

Thus, an aspect of the invention provides a base elate having an array of holes that extend therethrough; a plurality of discrete pins, each pin having an upper end and a lower end and being freely slidingly received in a corresponding hole in the base plate for independent reciprocating motion between a fully extended lowered position and a predetermined retracted raised position; and a free floating weight plate resting on the upper ends of the pins to bias the tins toward the fully extended lowered position with means for guiding the weight plate during vertical movement thereof.

Figure 8:
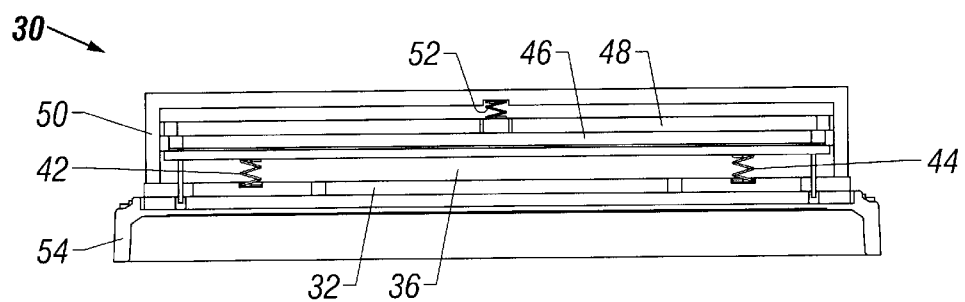
FIG. 8 is a vertical sectional view of a second embodiment of the present invention taken along line 8—8 of FIG. 9. The pins are not illustrated for the sake of clarity.
Figure 9:
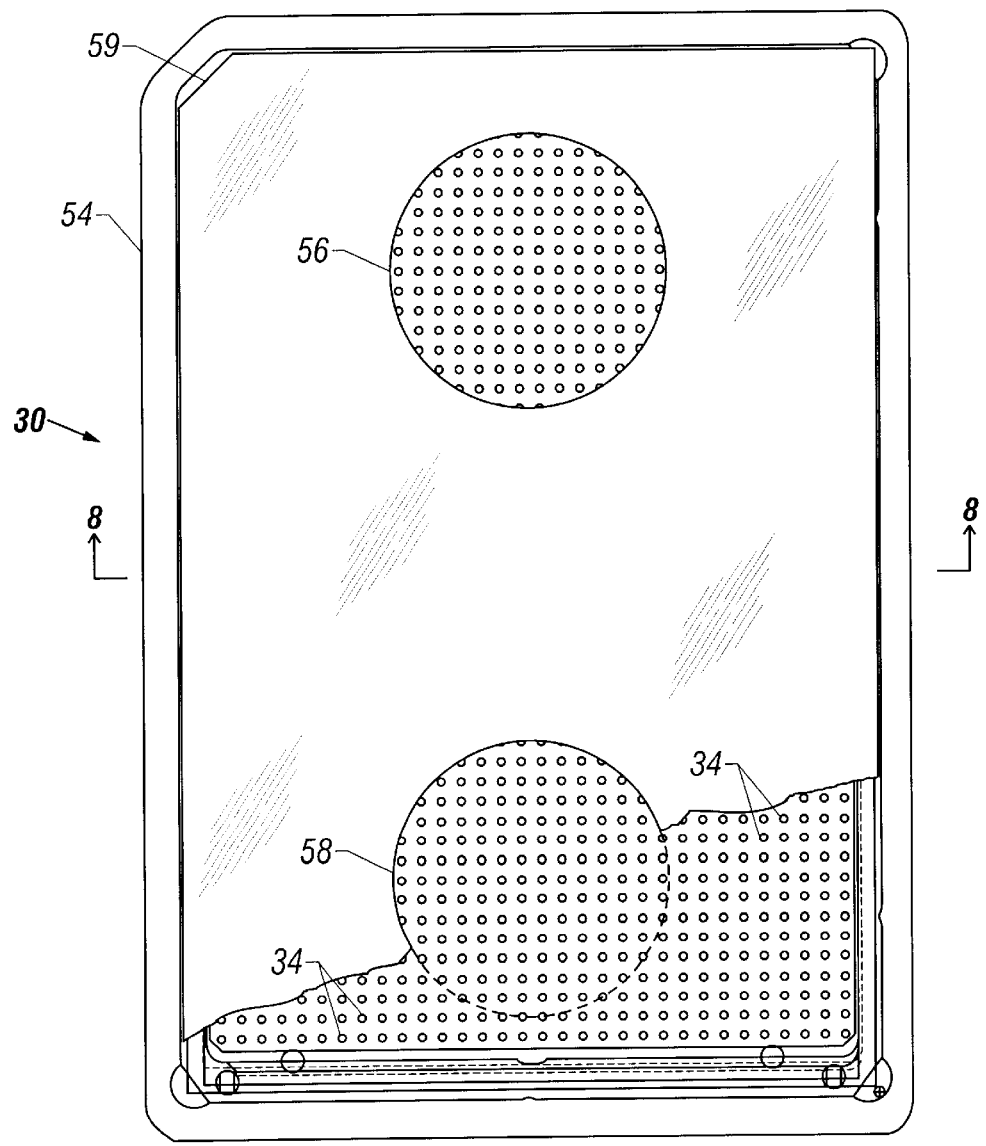
FIG. 9 is a top fragmentary plan view of the second embodiment with the weight plate and foam layer removed.
Figure 10:
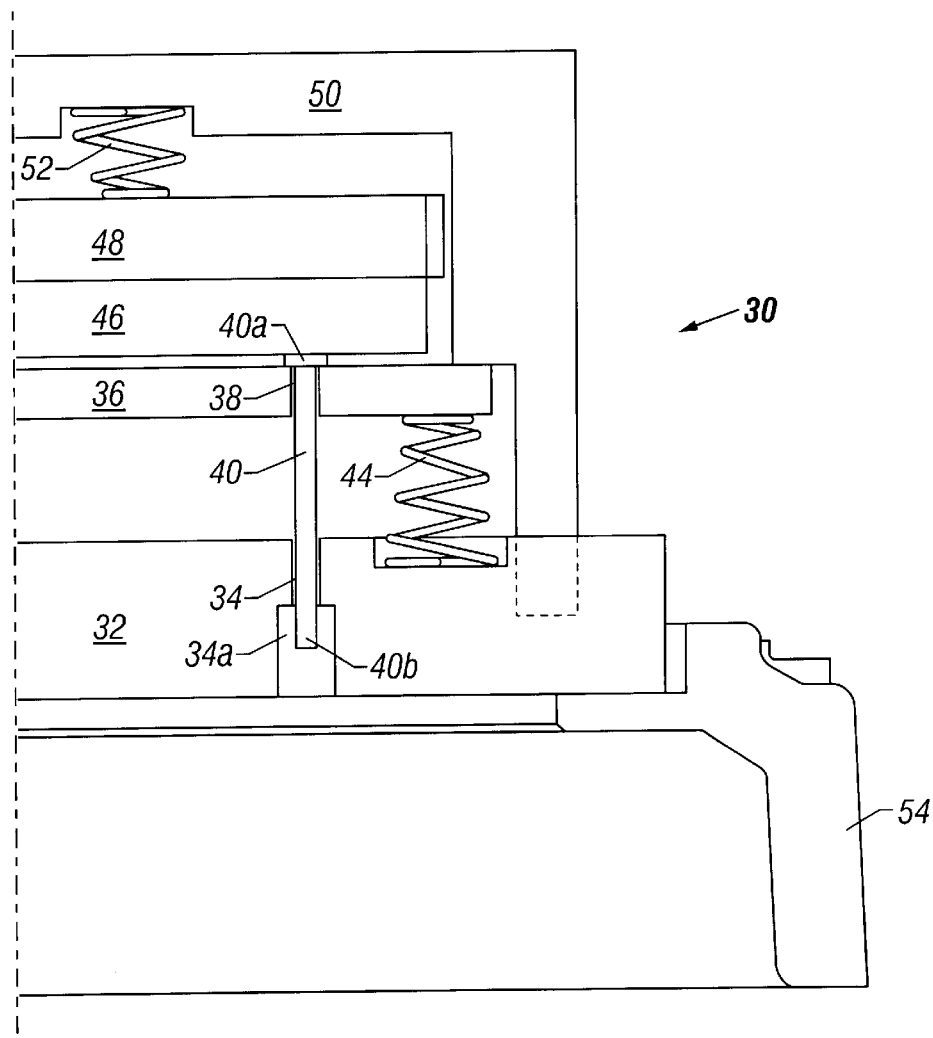
FIG. 10 is an enlarged, fragmentary illustration of the second embodiment.

Referring to FIGS. 8–10 second embodiment 30 of our pin transfer assembly includes a base plate 32 having a first array of holes 34 (FIG. 9) that extend therethrough. A spring plate 36 (FIGS. 8 and 10) is positioned above the base plate 32 and has a second array of holes 38 (FIG. 10) that extend therethrough. The second array of holes 38 in the spring plate 36 is complementary in number and arrangement to the first array of holes 34 in the base plate 32. A plurality of headed pins 40 (FIG. 1) each having an upper end 40a and a lower end 40b are slidingly received in corresponding holes in the first array of holes 34 in the base plate 32 and corresponding holes in the second array of holes 38 in the spring plate 36. The pins 40 are capable of reciprocating motion between a fully extended lowered position and a fully retracted raised position. The holes 34 and 38 in the base plate 32 and spring plate 36, respectively, are preferably drilled to provide a higher degree of tolerance control between the outer diameter of the pins 40 and the inner diameters of the holes 34 and 38. By having the shafts of the pins 40 slide through holes in two space apart planar members the lower ends 40b of the pins are less subject to minute lateral displacements that could lead to errors in picking up or depositing minute amounts of liquid, i.e. there is less chance for cross-contamination.

The base plate 32 and the overlying spring plate 36 are biased apart by a plurality of coil springs 42 and 44 (FIG. 8) locate around the periphery of the base plate 32. A layer 46 (FIGS. 8, 9 and 10) of a compressible material, such as a polyurethane foam having suitable density and memory, overlies the heads 40a of the pins 40. A weight plate 48 (FIGS. 8 and 10) rests on top of the layer 46. of compressible material. A box-like cover 50 (FIGS. 8 and 10) is attached around a periphery thereof to a periphery of the base plate 32. The cover 50 encloses the weight plate 48, the layer 46 of compressible material and the spring plate 36. The cover 50 is configured to guide the weight plate 48 during vertical movement thereof The spring plate 36 is guided by the pins 40. The combination of the location of the holes 34 in the base plate 32 and holes 38 in the spring plate 36 targets the lower ends 40b of the pins 40 at the appropriate locations. A single coil spring 52 (FIGS. 8 and 10) is positioned between a center of the weight plate 48 and the cover 50 to push the weight plate 48 downwardly. A rectangular frame 54 (FIGS. 8–10) supports the periphery of the base plate 32 for predetermined alignment of the pin transfer assembly in a receptacle of a manual or automated machine. The lower portions of the holes 34 in the base plate 32 are formed with counterbores 34a (FIG. 10) to prevent liquid from contacting the base plate 32 when the pins 40 move upwardly therethrough. The upper portions of the holes 38 in the spring plate may be provided with counterbores (not illustrated) sized to receive the heads 40a of the pins 40 so that the upper surfaces of the pin heads 40a are flush with the upper surface of the spring plate 36 when the pins 40 are in the positions illustrated in FIG. 10. The springs 42 and 44 suspend the spring plate 36 and pins 40 above their respective fluid targets.

A pair of apertures 56 and 58 (FIG. 9) are formed in the cover 50 for permitting a user to push the weight plate 48 downwardly with his or her thumb or finger. Alternatively, push members of an automated machine can press on the weight plate 48 through the apertures 56 and 58 in the cover 50. The pins 40 are biased to an intermediate position between their fully extended lowered positions and their fully retracted raised positions. The second embodiment 30 has an advantage over the first embodiment 10 in that it allows the assembly to be moved toward the target or pick up location at an angle before being positioned so that the base plate 32 is parallel to the plane of the target without risk of any of the lower ends of the pins 40 contacting the liquid in the micro titer wells prematurely. Once the weight plate 32 and the spring plate 36 are depressed and lowered, pushing the pins 40 through the base plate 32 to their fully extended lowered positions, the springy, yielding property of the foam layer 46 ensures that different pins 40 can individually move upwardly slight amounts in order to accommodate non-co-planarity at the pick up or receiving ends of the liquid transfer process.

The peripheral edges of the cover 50 could be formed with projections (not illustrated) that extend into blind holes (not illustrated) in the peripheral edges of the base plate 32. These projections could be configured to lock into engagement. Alternatively, adhesive or sonic welding could be utilized. Pins (not illustrated) formed on the peripheral edges of the cover 50 could be press fit or heat staked into recesses (not illustrated) in the periphery of the base plate 32. Similar joining techniques could be utilized between the periphery of the base plate 32 and the frame 54. The second embodiment 30 has a diagonally truncated upper left outer corner 59 visible in FIG. 9 which assists in proper orientation of the base plate 32 to the frame 54. The outer edges of the base plate 32 are machined with precision straight edges to accurately locate and register into frame 54 which may have precision locator projections (not illustrated).

Figure 11:
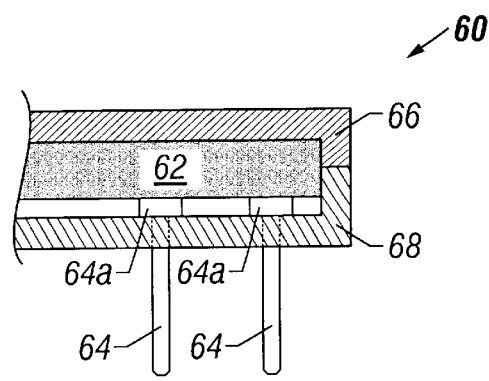
FIG. 11 is a fragmentary vertical sectional view of a third embodiment of the present invention.

FIG. 11 illustrates a third embodiment 60 of our pin transfer assembly that is less complex than the first two embodiments and therefore less expensive to manufacture. In the third embodiment the spring plate 36, weight plate 48 and coil springs 42, 44 and 52 of the second embodiment 30 are eliminated. A foam layer 62 is positioned between the array of reciprocable pins and the cover 66 for biasing the pin heads 64a toward the base plate 68.

All three embodiments of our pin transfer assembly described above share an important feature, namely, they each include a common means for biasing each of the pins toward a predetermined vertical position. This common biasing means enables our pin transfer assembly to accommodate non-co-planarity at either the pick up or deposit ends of the liquid transfer process. While we have described several preferred embodiments of our novel pin transfer assembly and a novel liquid transfer method, it should be apparent to those having ordinary skill in the art that our invention can be modified in both arrangement and detail. For example, the pattern of the pins can be varied. The pins could be hollow and they can be made of metal or plastic, or any other suitable material. The pins 40 can have different diameters, e.g., 0.012, 0.018, 0.025, 0.032 or 0.040 inches in diameter, to allow for different quantities of fluid to be transferred. The pin transfer assemblies need not be used with well plates but can be used with any source and target suitable for maintaining the separate physical integrity of the different liquid samples. Our pin transfer assemblies can be used in a manually operable jig or in an advanced computer—controlled robotic system. They can be inexpensively manufactured so that they can be made disposable. Alternatively, they may be made of stainless steel components so that they can be washed, sterilized, and re-used. Therefore, the protection afforded our invention should only be limited in accordance with the scope of the following claims.

We claim:

1. A pin transfer assembly for transferring minute quantities of liquids by means of surface tension of liquid between two different locations, comprising:

a base plate having an of holes that extend therethrough;

a plurality of pins, each pin having an upper end and a lower end and being slidingly received in a corresponding hole in the base plate, the pins being each freely-slideable in its corresponding hole fix reciprocating motion between a fully extended lowered position and a predetermined fully retracted raised position; and common means for biasing each of the pins toward the lowered position.

2. The pin transfer assembly of claim 1 wherein the upper end of each pin comprises a bead that abuts the base plate when the pin is in its fully extended lowered position.

3. The pin transfer assembly of claim 1 wherein the army of holes provides a pattern of rows and columns of pins.

4. The pin transfer assembly of claim 1 wherein the common biasing means further includes a weight plate that engages the upper ends of the pins and spring means for biasing the weight plate downwardly again the upper ends of the pins.

5. A pin assembly for transferring minute quantities of liquids between two different locations, comprising:

a base plate having a first array of holes that extend therethrough;

a spring plate positioned above the base plate and having a second array of holes that extend therethrough, the second array of holes in the spring plate being complementary in number and arrangement to the first array of holes in the base plate;

a plurality of pins, each in having an upper end and a lower end and being slidingly received in a corresponding hole in the first army of holes in the base plate and a corresponding hole in the second array in the second array of holes in the spring plate for reciprocating motion between a fully extended lowered position and a fully retracted raised position;

a layer of a compressible material overlying the upper ends of the pins;

a weight plate resting on of the layer of compressible material;

a cover overlying the weight plate and attached around a periphery thereof to a periphery of the base plate and enclosing the weight plate, layer of compressible material and spring plate, the cover being configured to guide the weight plate during vertical movement thereof;

spring means positioned between the base plate and the spring plate for biasing the spring plate upwardly.

6. The pin transfer assembly of claim 5, wherein the upper end of each pin comprises a head that abuts the spring plate when the pin is in its fully extended lowered position.

7. The pin transfer assembly of claim 5, wherein the first and second arrays of holes provides a pattern of rows and columns of pins.

8. The pin transfer assembly of claim 5, and further comprising a frame that supports the periphery of the base plate for predetermined alignment of the pin transfer assembly in a receptacle.

9. The pin transfer assembly of claim 6, wherein the holes in the base plate are formed with counterbores to prevent liquid from contacting the base plate when the pins move upwardly therethrough.

10. The pin transfer assembly of claim 6, and further comprising second spring means positioned between the weight plate and the cover for biasing the weight plate downwardly.

11. The pin transfer assembly of claim 5, and further comprising at leas one aperture formed in the cover for permitting a user to push the weight plate downwardly with his or her thumb or finger.

12. The pin assembly of claim 5, wherein the spring means includes a plurality of coil springs positioned around the periphery of the base plate.

13. The pin transfer assembly of claim 10, wherein the second spring means comprising a single coil spring positioned in a middle area of the weight plate.

14. A method of transferring minute quantities of a sample liquid between two different locations for further analysis, comprising the steps of:

providing a generally planar pin transfer assembly having an array of vertically reciprocable pins commonly biased to a lowered extended position;

positioning the pin transfer assembly horizontally above a first location;

moving the pin transfer assembly downwardly toward the first location so that a lower end of each of the pins contacts a sample liquid a sufficient amount to pick up and retain a small quantity of the sample liquid, while ensuring co-planarity of the lower ends of the pins by pushing each pin downwardly to a fully extended lowered position while allowing each pin to move upwardly should it contact an upper surface of the first location;

moving the pin transfer assembly upwardly away from the lint location;

moving the pin transfer assembly laterally to a horizontal position above a second location;

moving the pin transfer assembly downwardly toward the second location so that a lower end of each of the pins is sufficiently close to the second location so that the small quantity of the sample liquid on the lower end of each of the pins contacts an upper surface of the second location; and moving the pin transfer assembly upwardly away from the second location;

whereby a portion of the small quantity of the sample liquid previously carried by the lower end of each of the pins will remain on the second location.

15. A pin transfer assembly for transferring minute quantities of liquids between two different locations each of which is located a plurality of laterally-spaced liquid receptacles arranged in a plane, comprising:

a base plate having a first array of laterally-spaced holes that extend therethrough;

a plurality of discrete pins, each pin having an upper end and a lower end and being slidingly received in a corresponding hole in the base plate, the pins being each freely-slideable in its corresponding hole for reciprocating motion between an extended lowered position and a retracted raised position;

common means for biasing each of the pins toward a lowered position such that the pins are each biased toward a lowered position irrespective of a possible non-co-planarity of the receptacles at each of the locations;

the lower end of each of the pins being capable of transferring a minute quantity of a liquid between receptacles at different locations by means of the surface tension of the liquid.

16. A pin transfer assembly for transferring minute quantities of liquids between two different locations each of which is located a plurality of laterally-spaced liquid receptacles arranged in a plane, comprising:

a base plate having a array of laterally-spaced boles that extend therethrough;

a plurality of discrete pins, each pin having an upper end and a lower end and being slidingly received in a corresponding hole in the base plate, the pins being each freely-slideable in its corresponding hole in parallel relationship for reciprocating motion between an extended lowered position and a retracted raised position;

common means for biasing each of the pins toward a lowered position, the common means for biasing comprising a layer of compressible material located in biasing relationship with the upper end of each of the pins such that the pins are each biased toward a lowered position irrespective of a possible non-co-planarity of the receptacles at each of the locations;

the lower end of each of e pins being capable of transferring a minute quantity of a liquid between receptacles the different locations by means of the surface tension of the liquid.

17. A pin transfer assembly for transferring minute quantifies of liquids between two different locations each of which is located a plurality of laterally-spaced liquid receptacles arranged in a plane as claimed in claim 16, further comprising;

an enclosure comprising a bottom, a top having an inside surface, and sides interconnecting the bottom and top, the base plate constituting the enclosure bottom with the upper ends of the pins extending inside the enclosure and the lower ends of the pins extendable through the base plate holes to the outside of the enclosure;

the layer of compressible material comprising a layer of foam material extending inside the enclosure generally parallel with the base plate and between the upper ends of the pins and the top inside surface.

18. A pin transfer assembly for transferring minute quantities of liquids between two different locations at each of which is located a plurality of laterally-spaced liquid receptacles arranged in a plane as claimed in claim 17, wherein;

the layer of compressible foam material is in biasing contact with the upper ends of the pins and in contact with the inside surface of the enclosure top.

19. A pin transfer assembly for transferring minute quantities of liquids between two different locations at each of which is located a plurality of laterally-spaced liquid receptacles arranged in a plane as claimed in claim 16, further comprising:

an enclosure comprising bottom, a top, and sides interconnecting the bottom and top, the base plate constituting enclosure bottom with the upper ends of the pins extending inside the enclosure an the lower ends of the pins extendable through the base plate holes to the outside of the enclosure;

a spring plate positioned the enclosure above and in spaced relationship with the base plate and having a second array of holes that extend therethrough, the second array of holes in the spring plate being complementary in number and arrangement to the first array of holes in the base plate, each pin extending through a hole in the base plate also extending through a complementary hole in the spring plate;

the upper end of each pin comprising a head that abuts the spring plate;

the layer of compressible material extending inside the enclosure generally parallel with the base plate and between spring plate and the enclosure top and in biasing relationship with the pin heads;

first spring means position between the base plate and the spring plate for biasing the spring plate upwardly such that the pins are in a raised position.

20. A pin transfer assembly for transferring minute quantities of liquids between two different locations at each of which is located plurality of laterally-spaced liquid receptacles arranged in a plane as claimed in claim 19, further comprising:

means for applying a force to move the spring plate toward the base plate such that the pins are positioned in their lowered position.

21. A pin transfer assembly for transferring minute quantities of liquids between two different locations at each of which is located a plurality of laterally-spaced liquid receptacles arranged in a plane as claimed in claim 20, further comprising:

a weight plate resting on top of the layer of compressible material;

second spring means positioned between the weight plate and the enclosure top for applying a biasing force on the weight plate toward the base plate but such that the pins are maintained in their raised position.

22. A pin transfer assembly for transferring minute quantifies of liquids between two different locations at of which is located a plurality of laterally-spaced liquid receptacles arranged in a plane as claimed in claim 21, wherein the layer of compressible material comprises a layer of foam material.

* * * * *

UNITED STATES PATENT AND TRADEMARK OFFICE
CERTIFICATE OF CORRECTION

PATENT NO. : 6,610,253 B2
DATED : August 26, 2003
INVENTOR(S) : Craig M. Kennedy et al.

Figure 3:
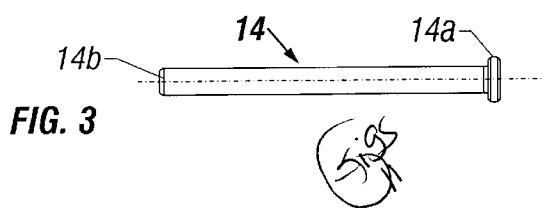
FIG. 3 is an enlarged side elevation view of one of the headed pins of the pin transfer assembly of FIG. 1.

It is certified that error appears in the above-identified patent and that said Letters Patent is hereby corrected as shown below:

Drawings,
The text/symbols below Fig. 3 should be deleted.

Column 6,
Line 41, "a bead" should be -- a head --.

Column 7,
Line 56, "lint" should be -- first --.

Signed and Sealed this

Second Day of December, 2003

JAMES E. ROGAN
*Director of the United States Patent and Trademark Office*